US006474159B1

(12) United States Patent
Foxlin et al.

(10) Patent No.: US 6,474,159 B1
(45) Date of Patent: Nov. 5, 2002

(54) MOTION-TRACKING

(75) Inventors: Eric Foxlin, Arlington, MA (US); Yury Altshuler, Chestnut Hill, MA (US)

(73) Assignee: Intersense, Inc., Burlington, MA (US)

( * ) Notice: Subject to any disclaimer, the term of this patent is extended or adjusted under 35 U.S.C. 154(b) by 0 days.

(21) Appl. No.: 09/556,135

(22) Filed: Apr. 21, 2000

(51) Int. Cl.$^7$ .............................................. G01P 15/00
(52) U.S. Cl. ........................................................ 73/488
(58) Field of Search ............................... 73/488, 503.3, 73/504.03, 570, 514.01; 600/587, 595; 128/897, 898, 774, 782; 367/117, 118; 33/333, 355 R

(56) References Cited

U.S. PATENT DOCUMENTS 5,645,077 A * 7/1997 Foxlin ......................... 128/774
6,176,837 B1 * 1/2001 Foxlin ......................... 600/595

OTHER PUBLICATIONS

E. Foxlin, "Head–tracking relative to a moving vehicle or simulator platform using differential inertial sensors", 2000.
E. Fuchs, "Inertial head–tracking", M.S. Thesis, Dept. of E.E.C.S., MIT, 1993.
E. Foxlin, "Inertial head–tracker sensor fusion by a complementary separate–bias kalman filter", Proc. VRAIS '96 Virtual Reality Annual Intl. Symposium, Santa Clara, CA 1996.
E. Foxlin et al., "Miniature 6–DOF inertial system for tracking HMDs", SPIE vol. 3362, Proc. AeroSense '98 Conference on Helmet– and Head–Mounted Displays III, Orlando, FL 1998.

InterSense Inc. homepage—http://www.isense.com.
K. Britting, "Inertial navigations systems analysis", New York, Wiley Interscience, 1971.
C. Broxmeyer, "Inertial navigation systems", New York, McGraw–Hill, 1964.
R. Parvin, "Inertial Navigation", Princeton, New Jersey, Van Nostrand, 1962.
R.G. Brown et al., "Introduction to random signals and applied Kalman filtering", 2$^{nd}$ edition, New York, John Wiley & Sons, 1992.

* cited by examiner

Primary Examiner—Helen Kwok
(74) Attorney, Agent, or Firm—Fish & Richardson P.C.

(57) ABSTRACT

Inertial trackers have been successfully applied to a wide range of head mounted display (HMD) applications including virtual environment training, VR gaming and even fixed-base vehicle simulation, in which they have gained widespread acceptance due to their superior resolution and low latency. Until now, inertial trackers have not been used in applications which require tracking motion relative to a moving platform, such as motion-base simulators, virtual environment trainers deployed on board ships, and live vehicular applications including helmet-mounted cueing systems and enhanced vision or situational awareness displays. to the invention enables the use of inertial head-tracking systems on-board moving platforms by computing the motion of a "tracking" Inertial Measurement Unit (IMU) mounted on the HMD relative to a "reference" IMU rigidly attached to the moving platform.

42 Claims, 7 Drawing Sheets

MOTION-TRACKING

BACKGROUND OF INVENTION

This invention relates to motion-tracking.

Inertial tracking with automatic drift correction has been demonstrated to be a successful technique for tracking objects, such as limbs, cameras, input devices, or head mounted displays (HMDs), offering low jitter, fast response, increased range, and reduced problems due to interference or line-of-sight occlusion. Inertial trackers have been successfully applied to a wide range of HMD applications including virtual environment (VE) training, virtual prototyping, interactive visualization and design, VR gaming, and even fixed-base vehicle simulation. Within this gamut of applications, inertial trackers have gained widespread acceptance as a high-performance, robust and cost-effective alternatives to magnetic, optical and acoustic tracking systems. InterSense of Burlington, Mass., has pioneered the commercial development of motion tracking systems using miniature MEMS-based inertial sensors, and now offers a broad product line of inertial hybrid trackers.

Until now, inertial trackers have not been used in applications that require tracking motion relative to a moving platform instead of relative to the earth. This includes such important applications as motion-base driving and flight simulators, conventional VE systems deployed on board ships, and a range of live vehicular applications such as driver's or pilot's vision enhancement, helmet-mounted cueing systems, and advanced human-machine interfaces to improve pilots' situational awareness and control capability. People wishing to use inertial trackers in these types of applications have been realized that standard inertial tracking systems such as the InterSense IS-300, 600 or 900 will not function correctly if operated on a moving platform such as a motion-base simulator or vehicle. The inertial sensors would measure head motion relative to the ground, while the drift-correcting range sensors would measure head pose relative to the vehicle platform in which the reference receivers are mounted. While the vehicle is turning or accelerating, the Kalman filter would attempt to fuse inconsistent data and produce unpredictable results.

SUMMARY OF INVENTION

The invention makes it possible to use inertial head-tracking systems on-board moving platforms by computing the motion of a "tracking" Inertial Measurement Unit (IMU) mounted on the object being tacked relative to a "reference" IMU rigidly attached to the moving platform. The advantages of the invention apply not only to inertial tracker with drift correction using ultrasonic ranging sensors, but also to hybrid inertial trackers involving optical, magnetic, or RF drift correction as well.

In general, in one aspect, the invention features a system for tracking the motion of an object relative to a moving reference frame. The system includes a first inertial sensor mounted on the tracked object; a second inertial sensor mounted on the moving reference frame; and an element coupled to the first and second inertial sensors and configured to determine an orientation of the object relative to the moving reference frame based on the signals from the first and second inertial sensors.

Implementations of the invention may include one or more of the following features. The first row and second inertial sensors may include three angular inertial sensors selected from the set of angular accelerometers, angular rate sensors, and angular position gyroscopes. The angular inertial sensors may include angular rate sensors, and the orientation of the object relative to the moving reference frame may be determined by integrating a relative angular rate signal determined from the angular rate signals measured by the first and second inertial sensors. A non-inertial measuring subsystem may make independent measurements related to the orientation of the object relative to the moving reference frame, and use them for correcting any drift that may occur in the inertial orientation integration. The non-inertial measuring subsystem may be selected from the set of optical, acoustic, magnetic, RF, or electromagnetic technologies.

The determination of relative orientation may be done by computing the orientation of the object with respect to a fixed inertial reference frame using the signals from the first inertial sensor, the orientation of the moving reference frame with respect to the same fixed inertial reference frame using the signals from the second inertial sensor, and the relative orientation based on the two orientations.

A drift corrector may be used to correct inertial drift in the determined orientation of the object with respect to the inertial reference frame or of the moving reference frame with respect to the inertial reference frame. The drift corrector may include sensors for determining tilt with respect to earth's gravitational field, heading with respect to earth's magnetic field. A drift corrector may be used for correcting inertial drift in the determined orientation of the object with respect to the moving reference frame by using non-inertial sensors to independently measure the relative orientation.

The first and second inertial sensors may each include three linear accelerometers. An element may be included for calculating the position of the object relative to the moving reference frame. The calculating element may double-integrate a relative linear acceleration signal computed from the linear accelerometer signals measured by the first and second inertial sensors. The calculation of the relative linear acceleration signal may include compensation for tangential, Coriolis and centripetal acceleration effects caused by the angular velocity and angular acceleration of the moving reference frame. The compensation terms may be calculated using the angular velocity or angular acceleration of the moving reference frame measured by the second inertial sensor. In some implementations no compensation for the effect of gravity on the accelerometers is made.

The calculation of the position of the object relative to the moving reference frame may include computing the position of the object with respect to a fixed inertial reference frame using the signals from the first inertial sensor, the position of the moving reference frame with respect to the same fixed inertial reference frame using the signals from the second inertial sensor, and the relative position based on the two individual positions. A drift corrector may correct for inertial drift in the determined position of the object with respect to the inertial reference frame or of the moving reference frame with respect to the inertial reference frame. The drift corrector may include sensors for measuring position of both the object and the moving reference frame with respect to landmarks fixed in common inertial reference frame. The moving reference frame may be associated with a vehicle, and the second inertial sensor may include a pre-existing inertial measurement unit on a vehicle that was installed for the purpose of navigation. The first and second inertial sensors may each include at least six linear accelerometers and associated processors to extract three angular inertial signals and three linear accelerations.

Other advantages and features will become apparent from the following description and from the claims.

DETAILED DESCRIPTION

1 Derivation of Kinematics 1.1 Inertial Tracking Relative to Fixed Platform

Figure 1:
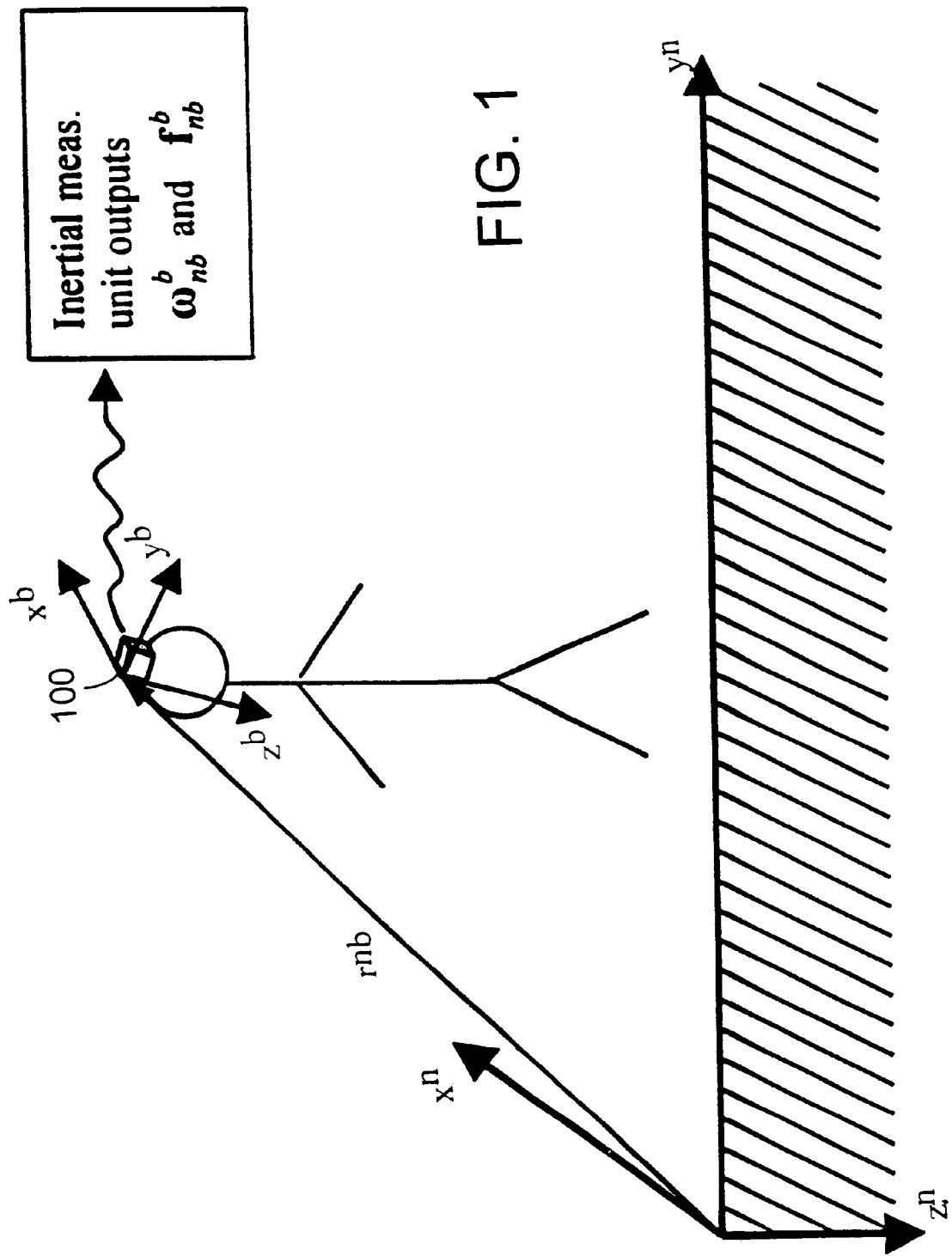
FIG. 1 shows inertial tracking relative to stationary ground.

FIG. 1 illustrates the case of using an inertial system 100 to track the pose of a body b, with respect to an inertially fixed navigation frame, n. In this situation, which represents the operation of InterSense's existing tracking products, there are only two coordinate frames used. Hereafter, vectors and matrices are designated with boldface characters, and superscripts, if present, indicate in which frame vectors are coordinatized. The subscripts on $r_{nb}$ indicate that it is the vector from the n-frame origin to the b-frame origin. Likewise $\omega_{nb}^b$ represents the angular rate vector of the b-frame with respect to (w.r.t.) the n-frame coordinatized in the b-frame, which is what the strapped-down triad of rate gyros aligned with the b-frame axes measures. The accelerometer triad senses $f_{nb}^b$, the non-gravitational acceleration (also known as specific force) of the b-frame w.r.t. the inertial reference frame, n, expressed in b-frame.

The orientation of the b-frame w.r.t. the n-frame can be conveniently represented using a direction cosine matrix $C_b^n$, which is simply the 3×3 rotation matrix that transforms vectors from b-frame to n-frame: $v^n = C_b^n v^b$. The orientation is integrated, starting from a known initial orientation matrix, using the differential equation:

$$\dot{C}_b^n = C_b^n S(\omega_{nb}^b), \quad (1)$$

where $S(\omega_{nb}^b) \equiv [\omega_{nb}^b \times]$ is the skew-symmetric matrix formed from the elements of $\omega_{nb}^b$ to implement the cross-product operator noted in the square brackets. The updated rotation matrix is then used to resolve the accelerometer readings into the n-frame, whence they can be easily corrected for the effect of gravity and double integrated to obtain the head position using:

$$\dot{v}_{nb}^n = C_b^n f_{nb}^b + g^n$$
$$\dot{r}_{nb}^n = v_{nb}^n \quad (2)$$

where $g^n \approx [0\ 0\ 9.8\ m/s^2]^T$ is the local apparent gravity vector which by definition points downward in navigation (nav) frame, and the derivatives are both calculated relative to nav frame.

Equations (1) and (2) are integrated numerically in the InterSense IS-600 processor to keep track of orientation, velocity and position. They may appear overly simple, but the gyro sensors in the InterSense InertiaCube™ IMU are not sensitive enough to detect the 15°/hr rotation of the earth, so there is no need to include terms to compensate for its effect on the sensors. The drift that results from using such low-performance gyros and neglecting the effects of earth rotation must be frequently corrected by other means, ultrasonic position sensors and a drift correction Extended Kalman Filter in the case of the IS-600.

1.2 Inertial Tracking Relative to Rotating Earth

In this section, we review the basic equations of terrestrial navigation, primarily as a source of inspiration for the derivation in the following section, which deals with a similar problem of tracking a moving body relative to another moving body.

Figure 2:
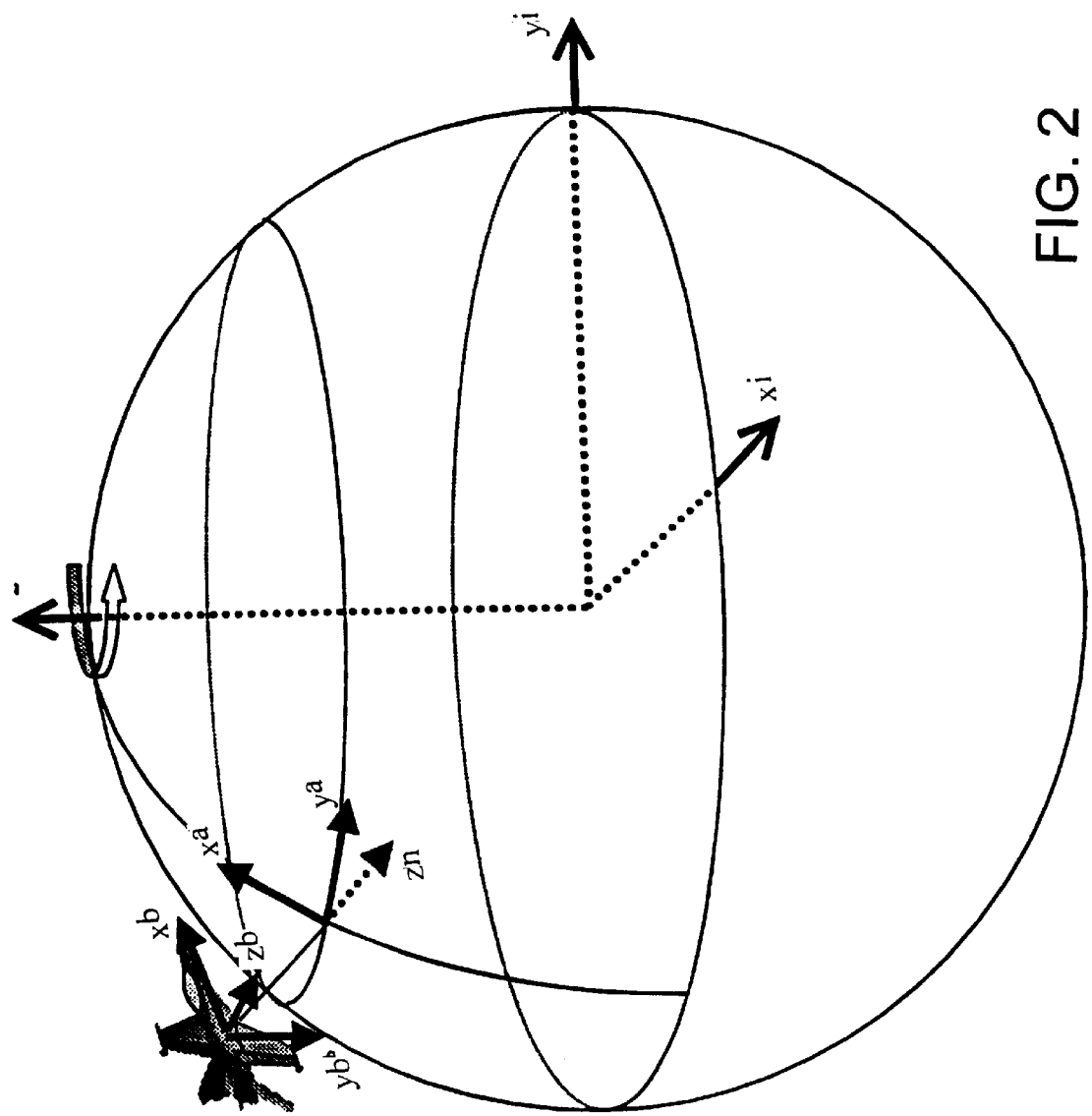
FIG. 2 shows inertial navigation relative to rotating earth.

Unlike the previous section, we will now need three coordinate frames. The inertial frame, or i-frame, has its origin at the center of the earth, but its axes do not rotate with the earth, rather they stay fixed with respect to the distant stars. The orbit of this frame about the sun is so slow that it is perfectly adequate to treat it as an inertial reference frame. Just as before, the body frame is defined fixed in the body being tracked, now an airplane, with the x-axis forward, y-axis right, and z-axis down. The navigation frame (n-frame) is now defined as a locally-level frame with its x,y,z-axes aligned to the local north, east and down directions respectively, as shown in FIG. 2. The down direction is defined by the local apparent gravity vector $g_l$, the direction a plumb bob hangs, which is the resultant vector of the mass attraction vector towards the earth and the centrifugal acceleration vector away from the earth rotation axis felt by an object stationary on the ground.

In real-life terrestrial navigation, the n-frame follows the aircraft around, having its origin always at the current aircraft position. Therefore, position and velocity cannot be specified with respect to n-frame, and it is necessary to introduce yet another frame, called e-frame, with its axes fixed in the earth. The usual strategy for aircraft navigation is to calculate the "groundspeed" $v_e$ relative to the earth, but coordinatize it in n-frame. This is convenient because 1) it is much easier to compute local gravity in n-frame, and 2) the north, east, and down velocities can be directly integrated to keep track of position in terms of lattitude, longitude and altitude, which are the desired coordinates for global navigation. However, for the present purposes, this adds some extra terms that are not needed for the derivation in the next section. For simplicity we will simply "freeze" the n-frame at a particular point on the earth, and assume that the plane flies around staying close enough to the origin of the n-frame that we can neglect curvature of the earth over this flying range.

We wish to track the airplane relative to the n-frame, which itself is moving relative to the inertial reference frame. The inertial measurement unit (IMU) on the airplane always measures the angular velocity and non-gravitational acceleration of the airplane relative to inertial space, expressed in b-frame: $\omega_{ib}^b$ and $f_{ib}^b$. Since $\omega_{ib} = \omega_{in} + \omega_{nb}$, we have $$\omega_{nb}^b = \omega_{ib}^b - C_n^b \omega_{in}^n, \quad (3)$$

which can be substituted into equation (1) and integrated to track the current orientation. $\omega_{ib}^b$ is available directly from the gyros, and $\omega_{in}^n$ can be calculated based on earth's rate and the latitude L. In the next section, where the n-frame is moving somewhat less predictably than the earth's rotation, $\omega_{in}^n$ cannot be calculated, but it can be directly measured by gyros mounted on the moving platform.

To find the aircraft's velocity and position relative to the n-frame, which is rotating relative to the inertial frame, we need to make use of the Law of Coriolis, which can be stated in it's most general form as $$D_a = D_b + \omega_{ab} \times \quad (4)$$

where $D_a$ represents an operator that differentiates any vector w.r.t. the a-frame, and a and b are any two Cartesian coordinate frames that share a common origin but are rotating with a relative angular velocity $\omega_{ab}$. Start with the equations of motion in the inertial frame, which are exceptionally straightforward:

$$D_i^2 r_{ib} = f_{ib} + g_m \quad (5)$$

This is a vector relationship, which will hold true in any coordinate frame, thus the lack of superscripts. $g_m$ represents a pure mass attraction gravity vector. We now wish to convert this n-frame. Expanding the left side of equation (5) with the Coriolis operator (4) we get:

$$\begin{aligned}
D_i^2 r_{ib} &= \{D_i^2 r_{in}\} + \{D_i^2 r_{nb}\} \\
&= \{(D_n + \omega_{in} \times)^2 r_{in}\} + \{(D_n + \omega_{in} \times)^2 r_{nb}\} \\
&= \{(D_n + \omega_{in} \times)(D_n r_{in} + \omega_{in} \times r_{in})\} + \{(D_n + \omega_{in} \times)(D_n r_{nb} + \omega_{in} \times r_{nb})\} \\
&= \{(D_n \omega_{in} \times r_{in} + \omega_{in} \times D_n r_{in} + \omega_{in} \times (\omega_{in} \times r_{in})\} + \{D_n^2 r_{nb} + D_n \omega_{in} \times r_{nb} + \omega_{in} \times D_n r_{nb} + \omega_{in} \times D_n r_{nb} + \omega_{in} \times (\omega_{in} \times r_{nb})\} \\
&= D_n^2 r_{nb} + 2(\omega_{in} \times D_n r_{nb}) + \omega_{in} \times (\omega_{in} \times (r_{in} + r_{nb})) \\
&= \dot{v}_{nb} + 2(\omega_{in} \times v_{nb}) + \omega_{in} \times (\omega_{in} \times r_{ib})
\end{aligned} \quad (6)$$

where terms containing $D_n \omega_{in}$ or $D_n r_{in}$ are dropped because $\omega_{in}$ and $r_{in}$ are constant vectors in the n-frame. Equating this to the right side of equation (5), we have $$\dot{v}_{nb} = f_{ib} + g_m - \omega_{in} \times (\omega_{in} \times r_{ib}) - 2(\omega_{in} \times v_{nb}) \quad (7)$$

$$= f_{ib} + g_l - 2(\omega_{in} \times v_{nb})$$

where $g_l \equiv g_m - \omega_{in} \times (\omega_{in} \times r_{ib})$ is the local apparent gravity caused by both mass attraction and centrifugal acceleration acting on the body due to earth's rotation. Gathering the results in one place, the navigation equations are:

$$\dot{C}_b^n = C_b^n S(\omega_{ib}^b - C_n^b \omega_{in}^n)$$

$$\dot{v}_{nb}^n = C_b^n f_{ib}^b + g_l^n - 2(\omega_{in}^n \times v_{nb}^n)$$

$$\dot{r}_{nb}^n = v_{nb}^n \quad (8)$$

which may readily be integrated using the inputs $\omega_{ib}^b$ and $f_{ib}^b$ from the aircraft IMU, plus the quantity $\omega_{in}^n$ which is calculated from earth rotation rate and the known latitude of the n-frame origin. Comparing to equations (1) and (2), these differ only by the addition of some extra terms to compensate for the effect of the rotation rate of the n-frame, $\omega_{in}^n$, on the gyros and accelerometers. These extra terms are tiny or slowly varying compared to the original terms. It is therefore traditional to integrate these terms at a rate much lower than the numerical integration rate of the larger terms, which is typically several hundred Hz.

1.3 Inertial Tracking Relative to an Arbitrary Maneuvering Platform

We track a person's head relative to a maneuvering platform by borrowing the mathematics that an inertial navigation system uses to track an airplane relative to a rotating earth, as outlined in the previous section. Some modifications will be required because the platform motion is more dynamic and unpredictable than the earth's rotation:

1) We cannot simply calculate $\omega_{in}^n$ based on the known constant earth rotation and latitude. Instead, we will have to attach a reference IMU to the platform and use its gyros to measure $\omega_{in}^n$.
2) We cannot use the $D_n \omega_{in}$ or $D_n r_{in} = 0$ simplifications.
3) Unlike the earth, the platform may be accelerating as well as rotating, so we must add terms to the navigation equation based on the reference IMU accelerometer readings.
4) Platform motion cannot be assumed slow, so all the terms must be included in the m-rate integration algorithms.
5) The motion platform is maneuvering unpredictably, and is no longer a locally-level reference frame. The apparent gravity vector does not always point straight down in the platform frame.

In light of these complications, one approach would be to use a locally level n-frame attached to the ground, and use the ground-relative tracking algorithm of section 1.1 to track both the motion platform (p) and the user's head (h) relative to the ground (n). Then the user's head pose relative to the motion platform can be computed using $C_h^p = C_n^p C_h^n$ and $r_{p \to h}^p = C_n^p (r_{n \to h}^n - r_{n \to p}^n)$.

Figure 3A:
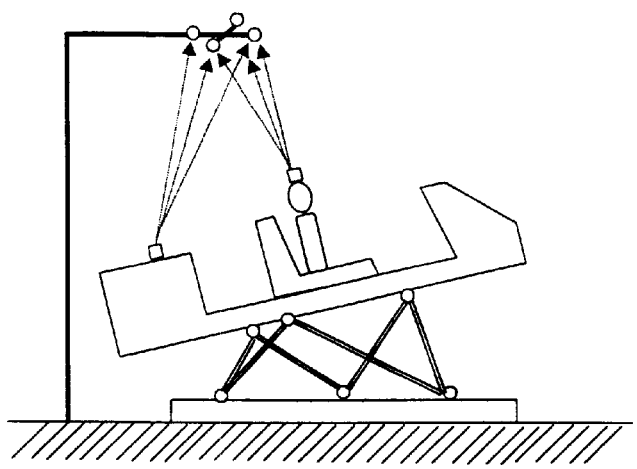
FIG. 3a shows tracking a platform and head relative to ground, using inertial and ground-relative absolute sensors.
Figure 3B:
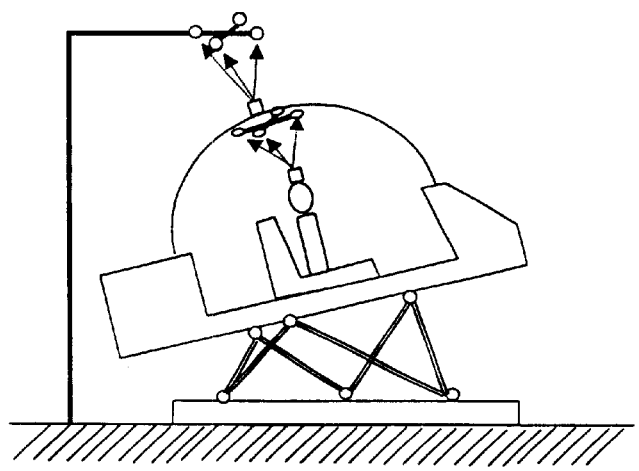
FIG. 3b shows tracking a platform relative to ground, and a had relative to ground (inertial) aided by platform-mounted sensors with known position relative to ground

Several engineers familiar with the operation of the IS-600 have suggested this approach. However, in many practical situations, there is a problem. The IS-600 normal tracking algorithm described in section 1.1 requires a clear acoustical path between the tracked object and the receiver X-bar for making the drift-correcting range measurements. This is fine for open-top motion-base simulators that are sometimes used with HMD-based systems, as illustrated in FIG. 3a. However, many motion-base simulators have closed-top simulator cabs, which would effectively prevent the use of acoustic, optical, or magnetic devices for providing auxiliary measurements of the head position relative to a receiver unit mounted at a fixed location outside the simulator cab. A possible solution to this problem is illustrated in FIG. 3b. Here again, both the head and platform inertial systems track relative to the ground, using the algorithms of Section 1.1. For the platform-tracker, the drift-correcting range measurements are made relative to an external X-bar fixed in the environment, as usual. For the head-tracker, aiding measurements relative to the ground are required to correct the inertial measurements, but the X-bar visible to the head-tracker is mounted on the moving simulator platform. To create virtual measurements relative to the ground, we could use the known simulator platform pose to transform the positions of the X-bar receiver pods into the fixed reference frame before processing their range measurements. In some cases, the external X-bar could be eliminated by utilizing data from encoders on the motion base actuators if they were available and could offer millimeter precision in real-time.

Figure 3C:
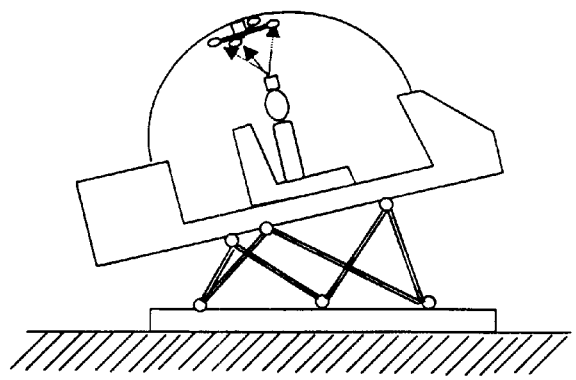
FIG. 3c shows tracking a head relative to a platform, using a self-contained system.

This may be a viable approach for some simulators, but it won't work for tracking on moving vehicles, where millimeter-level vehicle position data is generally not available. In vehicular tracking applications (and most simulators too), all that is required is the head pose relative to the moving platform. It would be desirable to find a method of measuring this pose directly, without having to track the vehicle with respect to the ground as well and to compute the pose difference afterwards. This would result in a general-purpose tracking system that would work with any type of moving platform, and the installation would be simpler because the whole system would be installed on the inside. FIG. 3c illustrates the hardware for such a system, installed in a motion-base simulator cab. In the remainder of this section, an approach is developed for doing this.

Figure 3D:
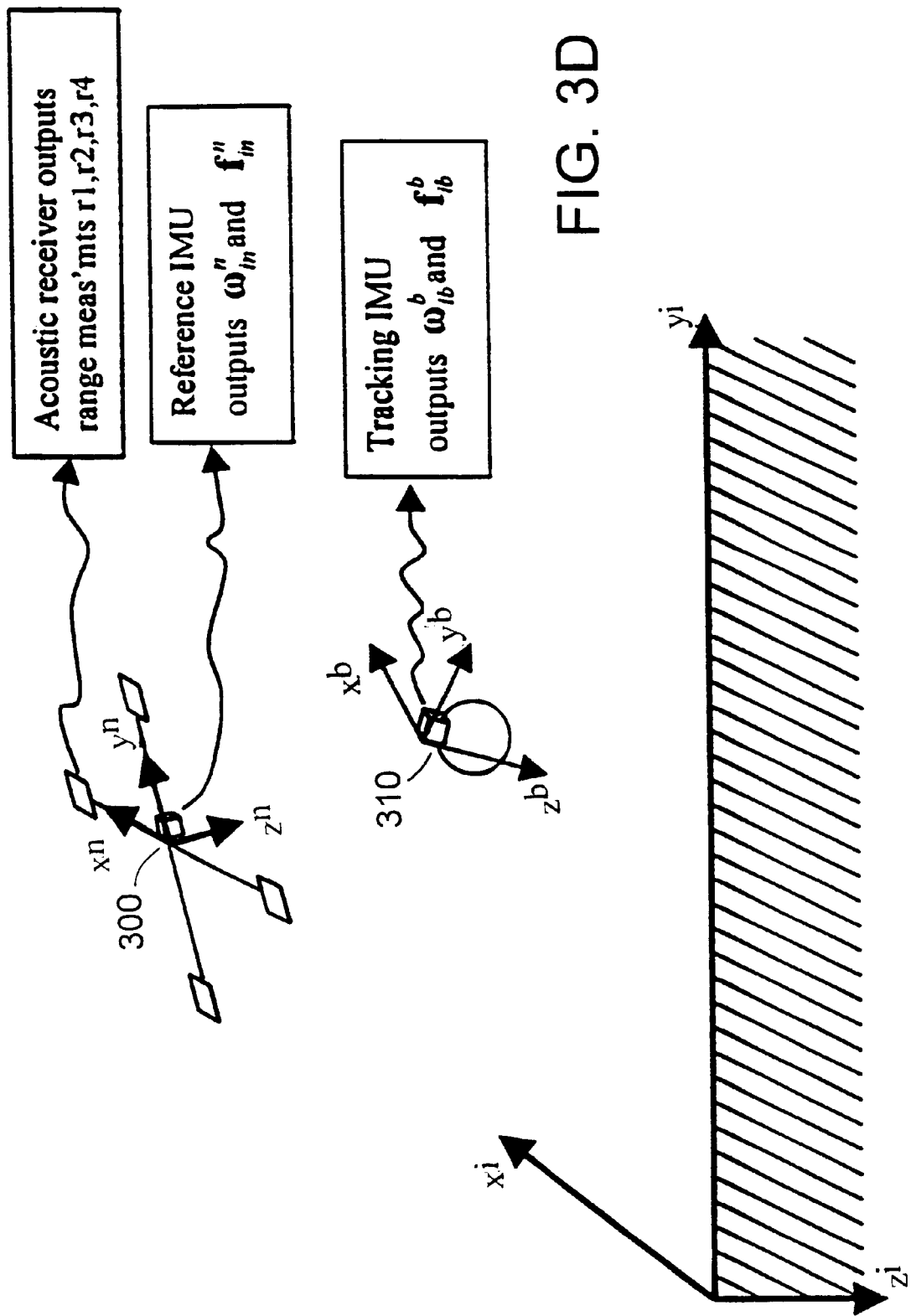
FIG. 3d shows coordinate system conventions for the relative tracking system of FIG. 3c.

The first step to achieving the desirable tracking system illustrated in FIG. 3c is to choose the navigation frame fixed to the moving platform. FIG. 3d illustrates a particularly convenient choice of n-frame axes, centered at the reference IMU 300 and aligned with its axes. The reference IMU is bolted to the center of an IS-600 X-bar (or any other reference tracking device), which in turn is bolted to the canopy of the simulator cab or cockpit. This may seem somewhat strange to those accustomed to inertial navigation systems, where the n-frame is always a locally-level frame with its vertical axis aligned with the direction of local gravity. The main purpose of the n-frame in fact is to provide a digital equivalent to an old-fashioned mechanically-gimbaled inertial navigation system (INS), in which gyros on the gimbals are used to servo-stabilize an accelerometer triad into a level and north-slaved attitude, even as the vehicle maneuvers about. With the accelerometers always held in this North-East-Down orientation, one need merely add 1 g to the output of the z accelerometer, then double integrate the accelerometer outputs to track position in the nav frame. In strapdown systems, the stored $C_b^n$ matrix is used to transform the accelerometer readings into nav-frame, then do exactly the same thing, as described in equation (2). To use this technique with the dancing n-frame illustrated in FIG. 3d, it may seem necessary to constantly keep track of $C_n^i$ (just what we are trying to avoid doing) in order to figure out the effect of local gravity in the n-frame and compensate for it. However, in one aspect of the invention, we provide an alternative.

We can use the reference IMU to measure the gravitational field in the n-frame at every time step, instead of trying to calculate it? The key that makes this approach possible is the realization that it is not necessary to explicitly compensate for the effect of earth's gravitation on the b-frame accelerometers. It is the combined effect of gravity and acceleration of the n-frame that disturbs the b-frame accelerometers and must be removed before integration. It happens that this summed effect is exactly what the reference IMU accelerometers measure. Using this observation to our advantage, we now repeat the derivation of Section 1.2, but without the luxury of canceling any terms due to constancy of n-frame rotation. Starting again with the universal i-frame frame equation of motion (5), we proceed in similar manner to equation (6), except we don't expand the $D_i^2 r_{in}$ term:

$$D_i^2 r_{tb} = D_i^2 r_{in} + \{D_i^2 r_{nb}\} \tag{9}$$

$$= D_i^2 r_{in} + \{(D_n + \omega_{in} \times)^2 r_{nb}\}$$

$$= D_i^2 r_{in} + \{(D_n + \omega_{in} \times)(D_n r_{nb} + \omega_{in} \times r_{nb})\}$$

$$= D_i^2 r_{in} + \{D_n^2 r_{nb} + D_n \omega_{in} \times r_{nb} + \omega_{in} \times D_n r_{nb} + \omega_{in} \times D_n r_{nb} + \omega_{in} \times (\omega_{in} \times r_{nb})\}$$

$$= D_i^2 r_{in} + \dot{v}_{nb} + \dot{\omega}_{in} \times r_{nb} + 2(\omega_{in} \times v_{nb}) + \omega_{in} \times (\omega_{in} \times r_{nb})$$

Using equation (5) to substitute both $D_i^2 r_{ib} = f_{ib} + g_m$ and $D_i^2 r_{in} = f_{in} + g_m$ and rearranging terms, we get $$\dot{v}_{nb}^n = C_b^n f_{ib}^b - \dot{\omega}_{in}^n \times r_{nb}^n - 2(\omega_{in}^n \times v_{nb}^n) - \omega_{in}^n \times (\omega_{in}^n \times r_{nb}^n) - f_{in}^n \tag{10}$$

where the orientation matrix $C_b^n$ comes from integrating $$\dot{C}_b^n = C_b^n S(\omega_{ib}^b - C_n^b \omega_{in}^n) \tag{11}$$

and position $r_{nb}^n$ is obtained by integrating $$\dot{r}_{nb}^n = v_{nb}^n \tag{12}$$

just as in Section 1.2.

If the reference IMU is mounted at the origin of the n-frame, then it directly measures $f_{in}^n$ and $\omega_{in}^n$, so (10) is the complete navigation equation, which can be integrated using just data available from the two IMUs. (A numerical approximation to the derivative of $\omega_{in}^n$ is needed if angular accelerometers are not available on the reference IMU.) The second, third and fourth terms are new additions compared to the stationary platform equation (2). They represent tangential, Coriolis, and centripetal accelerations respectively which result from the rotation of the n-frame. The Coriolis and centripetal terms are also present in the rotating earth navigation equation (8), with the latter being absorbed inside the definition of local gravity. The tangential acceleration term requires noise-boosting numerical differentiation of the discrete-time gyro outputs, and so could be a potential source of significant integration error if the lever arm $r_{nb}^n$ from the reference IMU 300 to the tracking IMU 310 is too long.

The fifth term, $-f_{in}^n$, replaces $g_l^n$, and incorporates both the effect of $g_m^i = [0\ 0\ g]^T$ rotated into the tilted n-frame as well as actual acceleration of the platform. By measuring the effect of gravity directly in the n-frame with a reference IMU, we do not need to know the platform tilt angles to resolve the gravity vector into the n-frame. Thus, this system operates independently without any inputs from the motion-base controller or the vehicle attitude reference system, and without the need to ever know or measure or calculate the orientation or position of the moving platform.

If the reference IMU is located at a non-zero offset position $r_{RIMU}^n$ from the n-frame origin, then it will measure $$\tilde{f}_{in}^n = f_{in}^n + D_I^2 r_{RIMU}^n) = f_{in}^n + \dot{\omega}_{in}^n \times r_{RIMU}^n \omega_{in}^n \times (\omega_{in}^n \times r_{RIMU}^n)$$

Therefore, we must first remove the effects of tangential and centripetal acceleration from $\tilde{f}_{in}^n$:

$$f_{in}^n = \tilde{f}_{in}^n - \dot{\omega}_{in}^n \times r_{RIMU}^n - \omega_{in}^n \times (\omega_{in}^n \times r_{RISMU}^n)$$

then pass this true $f_{in}^n$ into the navigation equation (10). This may add additional computation and numerical errors, which could be avoided by defining the n-frame origin at the reference IMU (as shown in FIG. 3d) and then subtract $r_{RIMU}^n$ from the final computed result $r_{nb}^n$.

2 Simulation Results 2.1 IS-600 MPT Configuration Description

Figure 4:
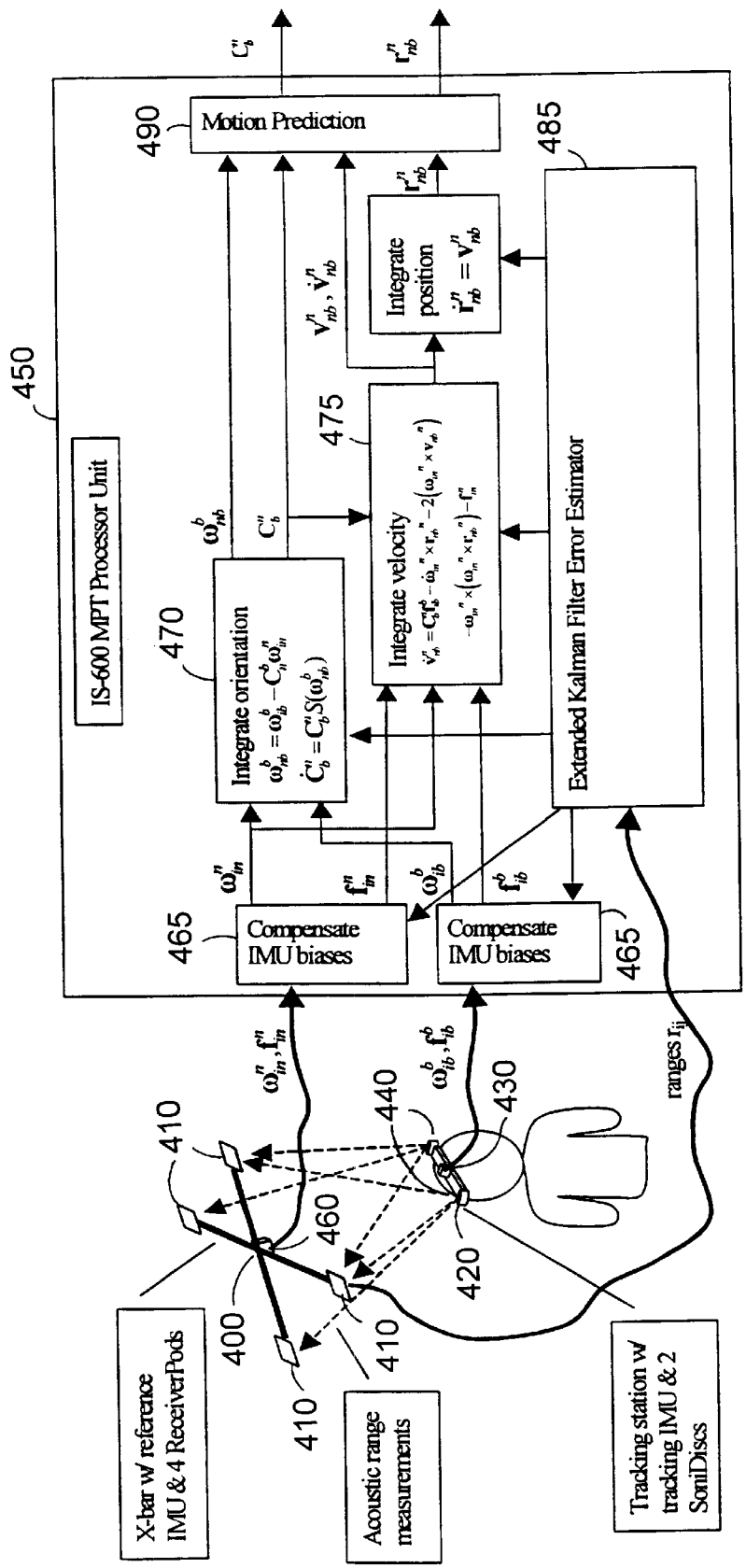
FIG. 4 shows an IS-600 MPT configuration and block diagram.

As an example of an implementation approach, we now define a specific tracking system configuration called IS-600 MPT. Referring to FIG. 4, the IS-600 MPT is a derivative of the InterSense IS-600 Mark 2 motion tracking system. Like the IS-600M2, the MPT has a reference X-bar 400 which holds four ultrasonic receiver pods 410, a tracking "station" 420 consisting of the tracking IMU 430 and two SoniDisc ultrasonic beacons 440 rigidly mounted on a strip about 6 inches long, and a rack-mount processor unit 450. The processor unit gathers the data from the various sensors, performs integration and sensor fusion algorithms, and outputs the cooked 6-DOF data to a host by serial port. The processor unit includes bias compensation units 465, an orientation integration unit 470 for integrating the orientation values, a velocity integration unit 475 for integrating velocity values, a position integration unit 480 for integrating position values. All of these units receive correction values generated by the extended Kalman filter error estimator unit 485. The values generated by these units are fed into the motion prediction unit 490, which generates predicted motion values. In addition, the IS-600 MPT has an additional reference IMU 460 mounted at the center of the X-bar where the default origin for the tracking reference frame (n-frame) is located. FIG. 4 illustrates the IS-600 MPT configuration as simulated in Section 2.3, including the enhanced kinematic integration algorithm derived in Section 1.3 for inertial tracking relative to a moving platform.

2.2 Bias Observability Problem

A careful examination of FIG. 4 reveals a potential problem with the proposed relative inertial tracking approach. One of the important tasks of the Extended Kalman Filter (EKF) error estimator is to estimate the inertial sensor biases, so that this information can be used to compensate the IMUs before performing the numerical integration of kinematics equations (11), (10), and (12). It is known that, for the case of fixed platform tracking using a single IMU, the complementary EKF formulation can successfully estimate and compensate for gyro biases. It is able to do this by indirectly observing the effect of the gyro biases on the propagation of orientation errors over time. Since a gyro bias on a particular gyro will cause orientation error to accumulate in a particular way, the filter can unequivocally trace back the orientation error to the offending gyro and correct its bias.

For the relative inertial tracking system of FIG. 4, there are actually 6 gyros contributing to the integration of the 3-DOF orientation through equation (11). For any particular orientation of the b-frame relative to n-frame, any number of gyro bias combinations might result in the same orientation drift pattern. For example, when the relative yaw, pitch and roll between the platform and the head are all zero, $C_n^b = I^{3 \times 3}$, and $\omega_{nb}^b = \omega_{ib}^b - \omega_{in}^n$. Equal gyro biases on the x-gyros of both IMUs would therefore cause the n-frame and b-frame to both rotate in the same direction so that the relative orientation would not change. Therefore, these nonzero gyro biases would be unobservable by a state estimator (EKF) that only receives measurements of the relative orientation of the two frames. Due to space limitations, we will not calculate the observability Grammian to prove this, but rather accept it intuitively. A similar problem exists for accelerometer bias observability while the two frames are in any particular fixed pose relative to one another.

Fortunately, it also seems intuitively reasonable that the observability problem will disappear as long as the b-frame is moving relative to the n-frame. Consider starting at the [0 0 0] relative orientation holding steady. After a moment, the state estimator will not know any of the individual gyro biases specifically, but it will know that the difference between the two x gyro biases is a certain value. Now suppose the b-frame suddenly rotates to yaw angle 90° relative to the n-frame. Now the tracking x-gyro is paired with the reference y-gyro and vice versa and the x and y-gyro biases of both IMUs will become observable. After another rotation about a different axis, the z-gyros will become observable as well. Therefore, it would seem that the tracker should still work as long as the user occasionally moves her head.

Whether this is acceptable or not depends on how frequently she must move her head in order to keep the tracking system performing within specifications. If the tracker only starts to degrade noticeably in performance half an hour after the user stops moving completely, this is unlikely to be a problem for most real applications. In the next section, a simulation is developed and used to experiment with the effect of user motion or lack thereof on tracking quality.

2.3 Simulation Results

A simulation has been written to evaluate the performance of the proposed algorithm, and the seriousness of the bias observability problem just described. The inputs to the simulation are two "truth" trajectory files, one describing the motion of the platform ($C_n^i(t)$ and $r_{in}^i(t)$), and the other describing the motion of the head relative to the platform ($C_b^n(t)$ and $r_{nb}^n(t)$). The simulation performs the following steps:

1) Calculates the "truth" motion of the head relative to i-frame from the two input files.
2) Calculates ideal reference IMU outputs $f_{in}^n$ and $\omega_{in}^n$ from the platform trajectory.
3) Calculates the ideal tracking IMU outputs $f_{ib}^b$ and $\omega_{ib}^b$ from the i-frame head motion found in step 1.
4) Corrupts both IMU outputs with realistic levels of noise and bias error, representative of InertiaCube performance.
5) Feeds these simulated IMU outputs, as well as simulated range measurements (also corrupted with an appropriate level of noise) through the IS-600 MPT processor algorithms as depicted in FIG. 4.
6) Plots the tracking system errors (the difference between the trajectory calculated by the simulated IS-600 MPT processor and the "truth" trajectory), together with the 1-sigma covariance bounds calculated by the EKF.

Figure 5:
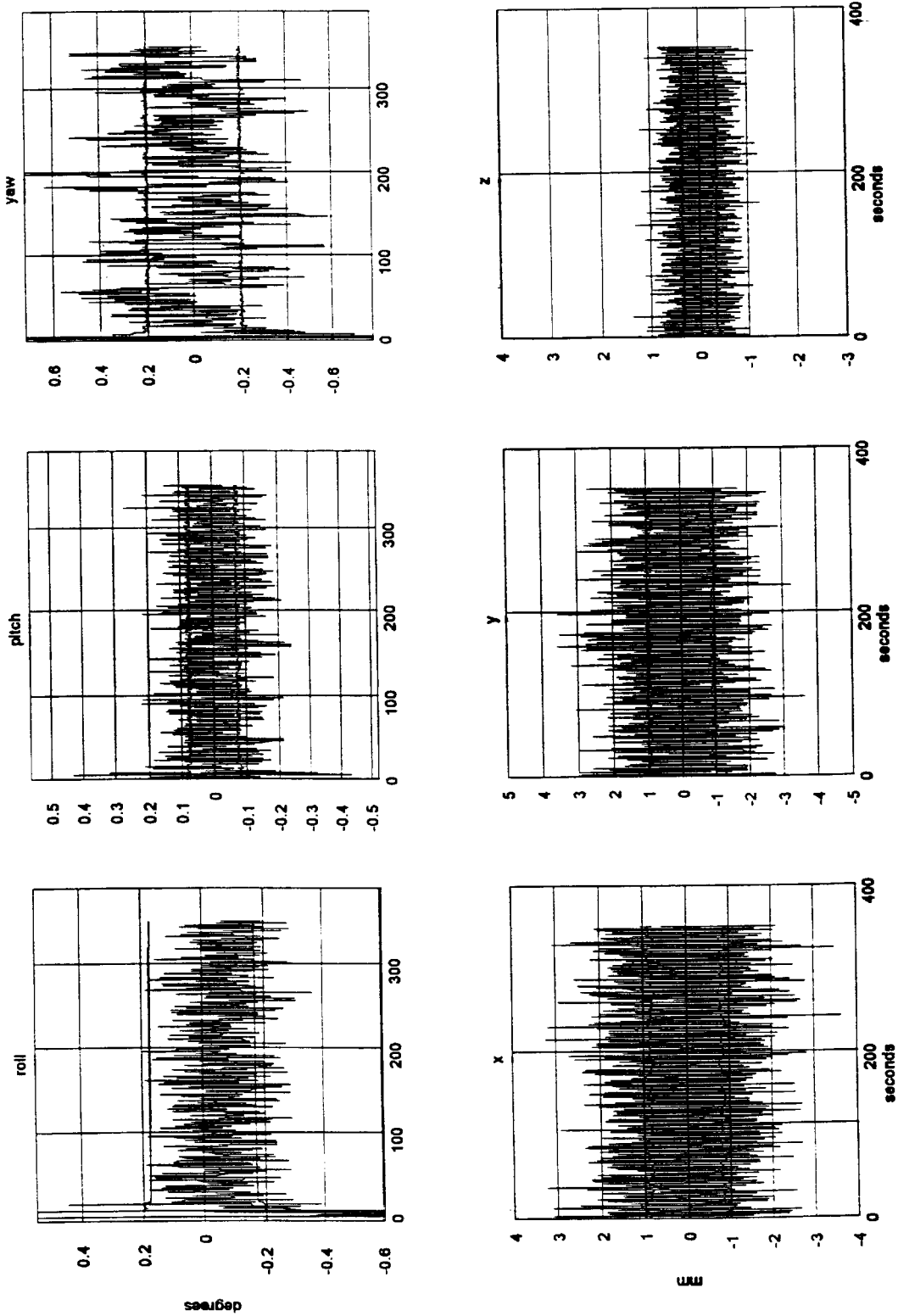
FIG. 5 shows simulated tracking errors and 1-sigma covariance bounds for a 6-minute run.

FIG. 5 shows the tracking system pose estimation errors (roll, pitch, yaw, x, y, and z errors) for a 6-minute run, simulated with a 30 Hz update rate. The platform trajectory had no motion. The head w.r.t. platform trajectory had a 30° yaw rotation (head shake) followed by a 30° pitch rotation (head nod) 10 seconds after the beginning of the simulation, and no motion thereafter. The tracking performance, approximately 0.2° rms in orientation and 1 mm rms in position, is only slightly degraded from an ordinary fixed platform IS-600 simulation with the same X-bar configuration and update rate. The interesting thing is that after the initial shake and nod, which were included to "get a fix" on the biases, the tracking continues for another 5½ minutes with no motion at all, and no noticeable increase in position or orientation errors.

Figure 6:
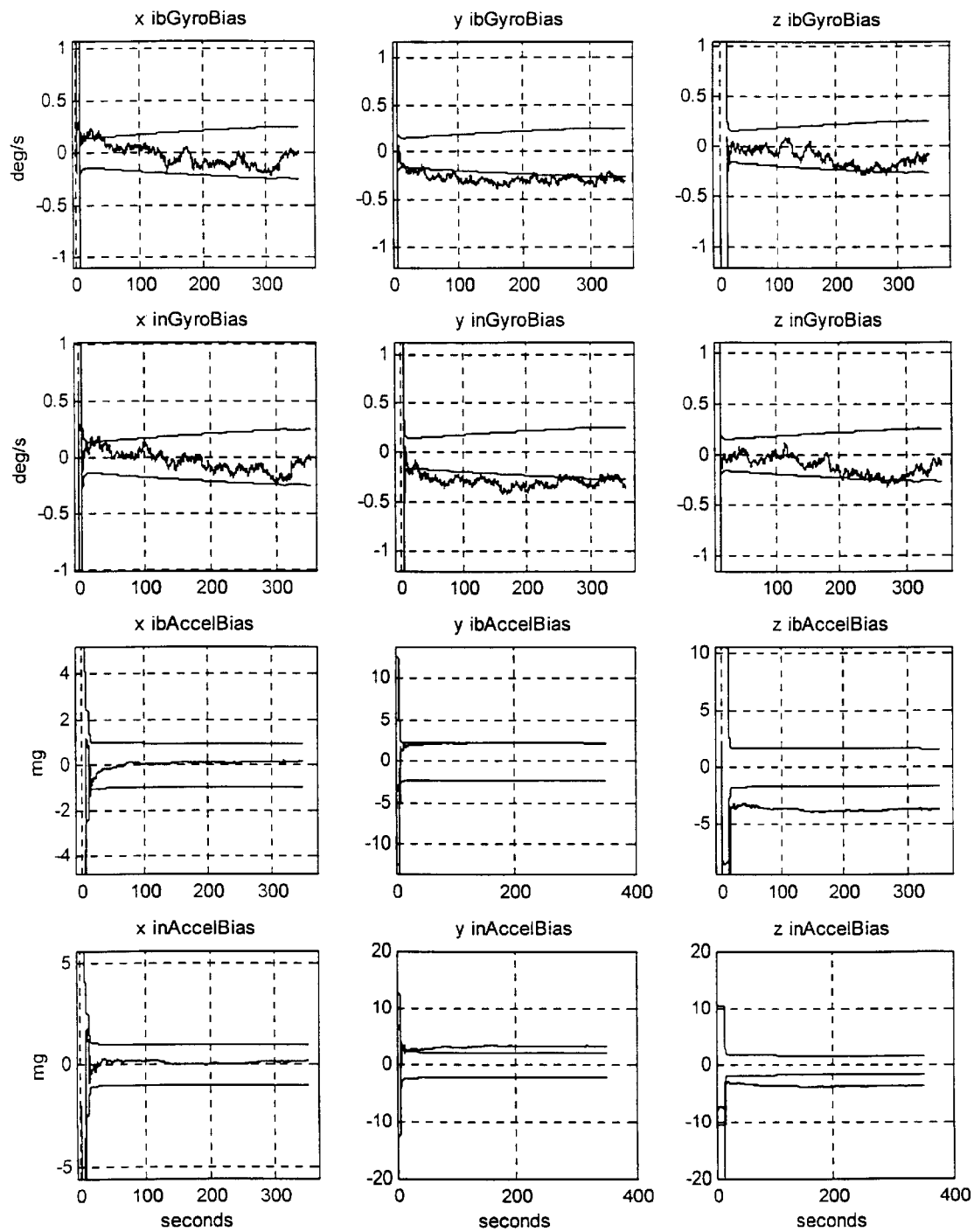
FIG. 6 shows simulated IMU bias estimation errors and 1-sigma covariance bounds for a 6-minute run.

FIG. 6 shows what happens to the bias estimation errors. As in FIG. 5, the differences between the filter-estimated biases and the actual biases that were used to corrupt the ideal IMU outputs are plotted, together with the filter-calculated 1-sigma covariance bounds on the bias states. If you zoom in on the beginning section of the graphs, you can see that initially the bias covariances stay approximately where they were initially set, because they are not yet observable. After the yaw rotation, the x and y gyro biases for both IMUs rapidly come down to normal operating levels. After the pitch rotation, the z biases also come down, all as we would expect from the observability discussion in Section 2.2. Over the remaining 5½ minutes, we see the gyro bias error covariances gradually climbing back upwards due to lack of observability during the motionless period. Interestingly, the increasing bias errors do not seem to have any significant effect on the pose estimation errors over this time period. It also appears that the accelerometer biases do not increase noticeably.

Another simulation run was performed to see how long good-quality tracking can be sustained with no user head-motion. Again, the head-motion trajectory began with a 30° shake/nod to set the biases, but then was followed by a half-hour of stillness, this time sampled at 5 Hz to keep the file sizes manageable. The same pattern emerged. The gyro biases (but not accelerometer biases) gradually crept up from the level they had been set to after the initial wiggle. By the end of a half-hour they had reached 0.5°/s, but still with no noticeable increase in the pose estimation error covariances. At that point, the trajectory contained a second wiggle, but this time only 10° in amplitude. This small wiggle of the head was sufficient to send the biases back down to 0.3°/s. From this it seems likely that the tracking will work fine as long as the user wiggles his head by at least 10° at least every half-hour. There is little point tracking a person's head if he is dead, so we don't consider this a very limiting requirement. Additional simulation runs have been performed which included motion of the platform, to confirm that the kinematic algorithms really work to extract only the relative motion. Indeed it was found that the errors in the relative tracking of the head w.r.t. the platform only increase slightly when the platform is flying tight figure-8's. This confirms that the relative navigation equations derived in Section 1.3 are correct, and that the Kalman filter model developed around them is working.

We have described a new approach to head-tracking on moving vehicles or motion-base simulator platforms, based on differential inertial sensing. This approach allows the benefits of inertially-based motion tracking to be realized on moving platforms, without the head-tracking accuracy being disturbed by the unpredictable motions of the platform. One feature of the described method is that it is self-contained: the tracking system does not need to be provided with any external information about the platform motion, and it can be installed locally inside the volume being tracked, just like an ordinary fixed-base tracking system.

Although the results have been illustrated using an acoustic/inertial hybrid tracking system configuration based on the InterSense IS-600, the basic concept is equally applicable with any other type of aiding measurements for the inertial sensors, including the magnetic or optical tracking systems that are currently used in many cockpit helmet-tracking applications.

Other embodiments are also within the scope of the following claims.

What is claimed is:

1. A system for tracking the motion of an object relative to a moving reference frame, comprising:
   a first inertial sensor mounted on the tracked object;
   a second inertial sensor mounted on the moving reference frame; and
   an element adapted to receive signals from said first and second inertial sensors and configured to determine an orientation of the object relative to the moving reference frame based on the signals received from the first and second inertial sensors.

2. The system of claim 1 in which the first and second inertial sensors each comprises three angular inertial sensors selected from the set of angular accelerometers, angular rate sensors, and angular position gyroscopes.

3. The system of claim 2, in which the angular inertial sensors comprise angular rate sensors, and the orientation of the object relative to the moving reference frame is determined by integrating a relative angular rate signal determined from the angular rate signals measured by the first and second inertial sensors.

4. The system of claim 3, further comprising a non-inertial measuring subsystem for making independent measurements related to the orientation of the object relative to the moving reference frame, and for using those measurements for correcting drift that may occur in the inertial orientation integration.

5. The system of claim 4, in which the non-inertial measuring subsystem is selected from the set of optical, acoustic, magnetic, RF, or electromagnetic technologies.

6. The system of claim 2, in which the determination of relative orientation includes
   computing the orientation of the object with respect to a fixed inertial reference frame using the signals from the first inertial sensor,
   computing the orientation of the moving reference frame with respect to the same fixed inertial reference frame using the signals from the second inertial sensor. and
   computing the relative orientation based on the two orientations.

7. The system of claim 6, further comprising a drift corrector for correcting inertial drift in the determined orientation of the object with respect to the inertial reference frame or of the moving reference frame with respect to the inertial reference frame.

8. The system of claim 7, in which said drift corrector includes sensors for determining tilt with respect to earth's gravitational field.

9. The system of claim 7, where said drift corrector includes sensors for determining heading with respect to earth's magnetic field.

10. The system of claim 6, further comprising a drift corrector for correcting inertial drift in the determined orientation of the object with respect to the moving reference frame by using non-inertial sensors to independently measure the relative orientation.

11. The system of claim 2, in which the first and second inertial sensors each further comprises three linear accelerometers.

12. The system of claim 11, further comprising an element for calculating the position of the object relative to the moving reference frame.

13. The system of claim 12, in which the calculating element double-integrates a relative linear acceleration signal computed from the linear accelerometer signals measured by the first and second inertial sensors.

14. The system of claim 13, in which the moving reference frame has an angular velocity and an angular acceleration, and wherein calculation of said relative linear acceleration signal includes compensation for tangential, Coriolis and centripetal acceleration effects caused by the angular velocity and angular acceleration of the moving reference frame.

15. The system of claim 14, in which the compensation for tangential, Coriolis and centripetal acceleration effects is calculated using the angular velocity or angular acceleration of the moving reference frame measured by the second inertial sensor.

16. The system of claim 13, in which no compensation for the effect of gravity on the accelerometers is made.

17. The system of claim 12, in which the calculation of the position of the object relative to the moving reference frame includes:
   computing the position of the object with respect to a fixed inertial reference frame using the signals from the first inertial sensor, computing the position of the moving reference frame with respect to the same fixed inertial reference frame using the signals from the second inertial sensor, and computing the relative position based on the position of the object and the position of the moving reference frame.

18. The system of claim 17, further comprising a drift corrector for correcting inertial drift in the determined position of the object with respect to the inertial reference frame or of the moving reference frame with respect to the inertial reference frame.

19. The system of claim 18, in which the drift corrector includes sensors for measuring position of both the object and the moving reference frame with respect to landmarks fixed in common inertial reference frame.

20. The system of claim 1, in which the moving reference frame is associated with a vehicle, and the second inertial sensor comprises a pre-existing inertial measurement unit on a vehicle that was installed for the purpose of navigation.

21. The system of claim 1, in which the first and second inertial sensors each comprises at least six linear accelerometers and associated processors to extract three angular inertial signals and three linear accelerations.

22. A method comprising determining an orientation of an object relative to a moving reference frame based on signals from two inertial sensors mounted respectively on the object and on the moving reference frame.

23. The method of claim 22 in which the two inertial sensors each comprise three angular inertial sensors selected from the set of angular accelerometers, angular rate sensors, and angular position gyroscopes.

24. The method of claim 23, in which the angular inertial sensors comprise angular rate sensors, and the orientation of the object relative to the moving reference frame is determined by integrating a relative angular rate signal determined from the angular rate signals measured by the first and second inertial sensors.

25. The method of claim 24, further comprising making independent measurements with a non-inertial measuring subsystem related to the orientation of the object relative to the moving reference frame, and using those measurements for correcting drift that may occur in the inertial orientation integration.

26. The method of claim 25, in which the non-inertial measuring subsystem is selected from the set of optical, acoustic, magnetic, RF, or electromagnetic technologies.

27. The method of claim 24, in which the determination of relative orientation includes computing the orientation of the object with respect to a fixed inertial reference frame using the signals from the first inertial sensor, computing the orientation of the moving reference frame with respect to the same fixed inertial reference frame using the signals from the second inertial sensor. and computing the relative orientation based on the two orientations.

28. The method of claim 27, further comprising using a drift corrector to correct inertial drift in the determined orientation of the object with respect to the inertial reference frame or of the moving reference frame with respect to the inertial reference frame.

29. The method of claim 28, in which said drift corrector includes sensors for determining tilt with respect to earth's gravitational field.

30. The method of claim 28, where said drift corrector includes sensors for determining heading with respect to earth's magnetic field.

31. The method of claim 27, further comprising using a drift corrector to correct inertial drift in the determined orientation of the object with respect to the moving reference frame by using non-inertial sensors to independently measure the relative orientation.

32. The method of claim 23, in which the first and second inertial sensors each further comprises three linear accelerometers.

33. The method of claim 32, further comprising calculating the position of the object relative to the moving reference frame.

34. The method of claim 33, in further comprising double-integrating a relative linear acceleration signal computed from the linear accelerometer signals measured by the first and second inertial sensors.

35. The method of claim 34, in which the moving reference frame has an angular velocity and an angular acceleration, and wherein calculation of said relative linear acceleration signal includes compensation for tangential, Coriolis and centripetal acceleration effects caused by the angular velocity and angular acceleration of the moving reference frame.

36. The method of claim 35, in which the compensation for tangential, Coriolis and centripetal acceleration effects is calculated using the angular velocity or angluar acceleration of the moving reference frame measured by the second inertial sensor.

37. The method of claim 34, in which no compensation for the effect of gravity on the accelerometers is made.

38. The method of claim 33, in which the calculation of the position of the object relative to the moving reference frame includes:

computing the position of the object with respect to a fixed inertial reference frame using the signals from the first inertial sensor, computing the position of the moving reference frame with respect to the same fixed inertial reference frame using the signals from the second inertial sensor, and computing the relative position based on the position of the object and the position of the moving reference frame.

39. The method of claim 38, further comprising using a drift corrector to correct inertial drift in the determined position of the object with respect to the inertial reference frame or of the moving reference frame with respect to the inertial reference frame.

40. The method of claim 39, in which the drift corrector includes sensors for measuring position of both the object and the moving reference frame with respect to landmarks fixed in common inertial reference frame.

41. The method of claim 22, in which the moving reference frame is associated with a vehicle, and the second inertial sensor comprises a pre-existing inertial measurement unit on a vehicle that was installed for the purpose of navigation.

42. The method of claim 22, in which the first and second inertial sensors each comprises at least six linear accelerometers and associated processors to extract three angular inertial signals and three linear accelerations.

* * * * *